(12) United States Patent
Guan et al.

(10) Patent No.: US 11,497,392 B2
(45) Date of Patent: Nov. 15, 2022

(54) EXTENDED DEPTH OF FIELD INTRAORAL IMAGING APPARATUS

(71) Applicant: CARESTREAM DENTAL LLC, Atlanta, GA (US)

(72) Inventors: Yiyi Guan, Pittsford, NY (US); Victor C. Wong, Pittsford, NY (US); James R. Milch, Penfield, NY (US)

(73) Assignee: Dental Imaging Technologies Corporation, Atlanta, GA (US)

( * ) Notice: Subject to any disclaimer, the term of this patent is extended or adjusted under 35 U.S.C. 154(b) by 0 days.

(21) Appl. No.: 17/204,332

(22) Filed: Mar. 17, 2021

(65) Prior Publication Data
US 2021/0267447 A1  Sep. 2, 2021

Related U.S. Application Data

(63) Continuation of application No. 16/310,674, filed as application No. PCT/US2016/037483 on Jun. 15, 2016.

(51) Int. Cl.
| | |
|---|---|
| *A61B 1/24* | (2006.01) |
| *A61B 1/00* | (2006.01) |
| *G01B 11/25* | (2006.01) |
| *G06T 5/00* | (2006.01) |
| *H04N 5/225* | (2006.01) |

(Continued)

(52) U.S. Cl.
CPC .......... *A61B 1/24* (2013.01); *A61B 1/00009* (2013.01); *A61B 1/00172* (2013.01); *A61B 1/00197* (2013.01); *G01B 11/2513* (2013.01); *G02F 1/0102* (2013.01); *G06T 5/003* (2013.01); *H04N 5/2256* (2013.01); *G02F 2203/50* (2013.01);

(Continued)

(58) Field of Classification Search
CPC ... A61B 1/24; A61B 1/00009; A61B 1/00172; A61B 1/00197; G01B 11/2513; G02F 1/0102; G02F 2203/50; G06T 5/003; G06T 5/20; H04N 5/2256; H04N 2005/2255; H05N 2005/2255
USPC .......................................... 348/66
See application file for complete search history.

(56) References Cited

U.S. PATENT DOCUMENTS

| | | | | |
|---|---|---|---|---|
| 2001/0045529 | A1* | 11/2001 | Iketaki ................. | G01J 3/4406 250/493.1 |
| 2010/0053350 | A1* | 3/2010 | Miyauchi ........... | G02B 27/0075 348/222.1 |

(Continued)

FOREIGN PATENT DOCUMENTS

| | | | |
|---|---|---|---|
| DE | 10 2009 017 801 A1 | 10/2010 | |
| EP | 2 213 223 A1 | 8/2010 | |

OTHER PUBLICATIONS

Translation of DE102009017801A1, Oct. 2010, see office action for citations. (Year: 2010).*

(Continued)

*Primary Examiner* — Matthew K Kwan
(74) *Attorney, Agent, or Firm* — Alston & Bird LLP

(57) ABSTRACT

An apparatus for intraoral imaging has an illumination source that directs light to an object. An imaging apparatus forms an image at an image sensor array from reflected light from the object, the imaging apparatus having an optical stop along an optical axis. A phase modulator is disposed at or near the optical stop. An image processor conditions data from the image sensor array and provides processed image data of the object.

18 Claims, 11 Drawing Sheets

(51) Int. Cl.
*G06T 5/20* (2006.01)
*G02F 1/01* (2006.01)

(52) U.S. Cl.
CPC ........ *G06T 5/20* (2013.01); *H04N 2005/2255* (2013.01)

(56) References Cited

U.S. PATENT DOCUMENTS

2010/0311005 A1* 12/2010 Liang ................ A61B 1/00009
 433/29
2013/0120532 A1 5/2013 Milch
2013/0120533 A1 5/2013 Milch
2017/0068134 A1* 3/2017 Yadin ................ G02F 1/134309

OTHER PUBLICATIONS

Dowski et al. ("Wavefront coding: a modern method of achieving high-performance and/or low-cost imaging systems", Oct. 1999), pp. 138, 143 and 144. (Year: 1999).*
Dowski, Jr., Edward et al., "Wavefront Coding: A modern method of achieving high performance and/or low cost imaging systems," Proceedings of SPIE—The International Society for Optical Engineering, 3779:137-145, (Jul. 1999).
WIPO Application No. PCT/US2016/037483, PCT International Preliminary Report on Patentability dated Dec. 18, 2018.
WIPO Appiication No. PCT/US2016/037483, PCT International Search Report dated Mar. 30, 2017.
WIPO Appiication No. PCT/US2016/037483, PCT Written Opinion of the international Searching Authority dated Mar. 30, 2017.
U.S. Appl. No. 16/310,674, filed Dec. 17, 2018, Abandoned.

* cited by examiner

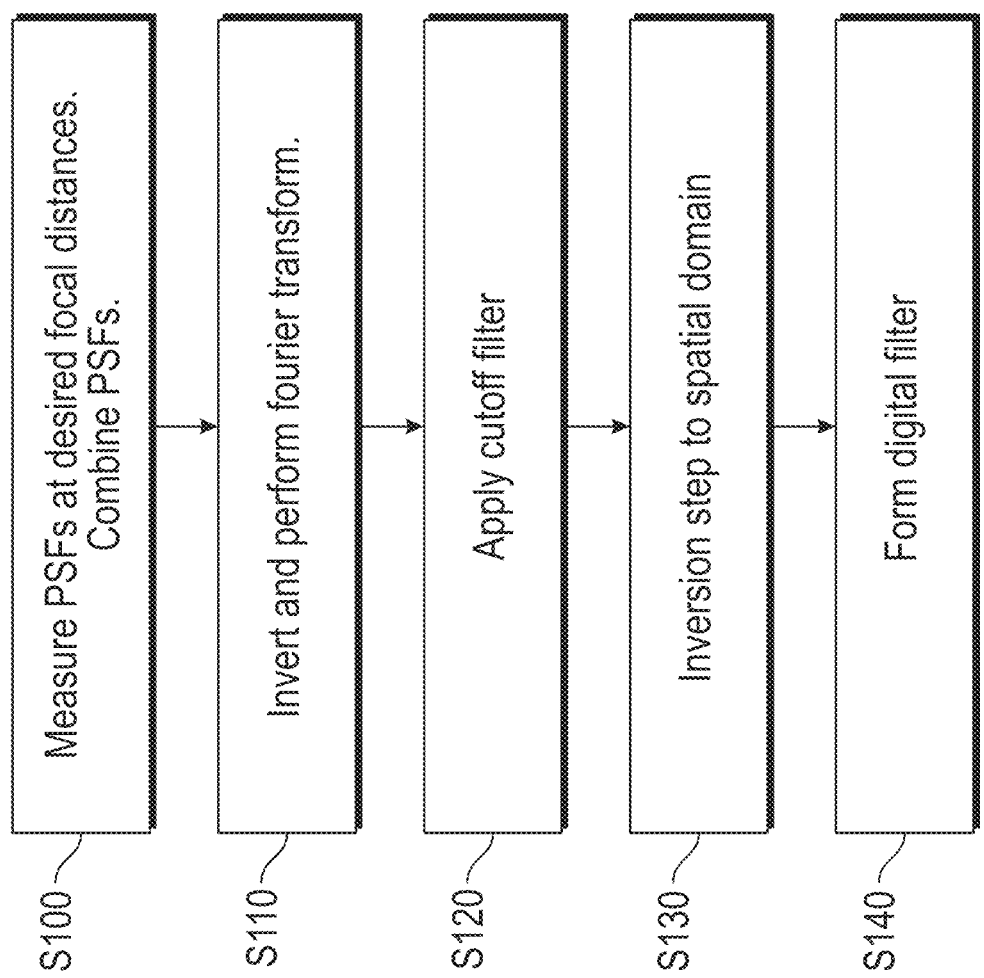

EXTENDED DEPTH OF FIELD INTRAORAL IMAGING APPARATUS

FIELD OF THE INVENTION

The disclosure relates generally to the field of dental diagnostic imaging and more particularly to an apparatus and method for intraoral scanning. The disclosure relates generally to methods and apparatus for intraoral imaging and more particularly to an intraoral imaging apparatus that has defocus correction to provide an extended depth of field.

BACKGROUND OF THE INVENTION

The intraoral camera is increasingly used as a diagnostic tool to support a range of applications for accurate characterization of shape and condition of teeth and supporting structures and tissues. In order to provide image content of sufficient resolution and accuracy for diagnostic use, the intraoral camera must meet demanding requirements for image quality.

The design of the portable, handheld intraoral camera must address a number of inherent challenges related to overall usability as well as to the constraints of the intraoral environment. The camera must be sized and shaped for ease of use and configured to allow access to different regions of the mouth. Sufficient illumination must be provided, within tight spacing and size constraints, for any type of reflectance imaging. This includes illumination for a camera that performs either contour imaging with patterned illumination or 2-D image acquisition with full-field imaging, or both.

One image aberration that can compromise image quality for the intraoral camera is defocus. Space and packaging constraints force camera optics to be of reduced size, even with the above-noted illumination constraints. Conventional methods for increasing the depth of field (DOF) and thereby reducing focus aberration cannot be applied without reducing illumination in a characteristically light-starved system.

Thus, it can be seen that there is need for improved solutions that increase the DOF of the intraoral camera without compromising the illumination levels available for imaging.

SUMMARY OF THE INVENTION

It is an object of the present disclosure to advance the art of diagnostic imaging and to address the need for improved imaging performance. An object of the present disclosure is to address the need for accurate characterization of intraoral surfaces. Exemplary method and/or apparatus embodiments in this application can relax requirements for positioning an intraoral imaging apparatus at the focal distance of an imaged tooth or other object.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to an aspect of the present disclosure, there is provided an apparatus for intraoral imaging that can include a) an illumination source that directs light to an object; b) an imaging apparatus that forms an image at an image sensor array from reflected light from the object, the imaging apparatus having an optical stop along an optical axis; c) a phase modulator disposed at or near the optical stop; and d) an image processor that conditions data from the image sensor array and provides processed image data of the object.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

FIG. 10 shows a sequence for forming a digital filter.

DESCRIPTION OF EXEMPLARY EMBODIMENTS

Figure 1:
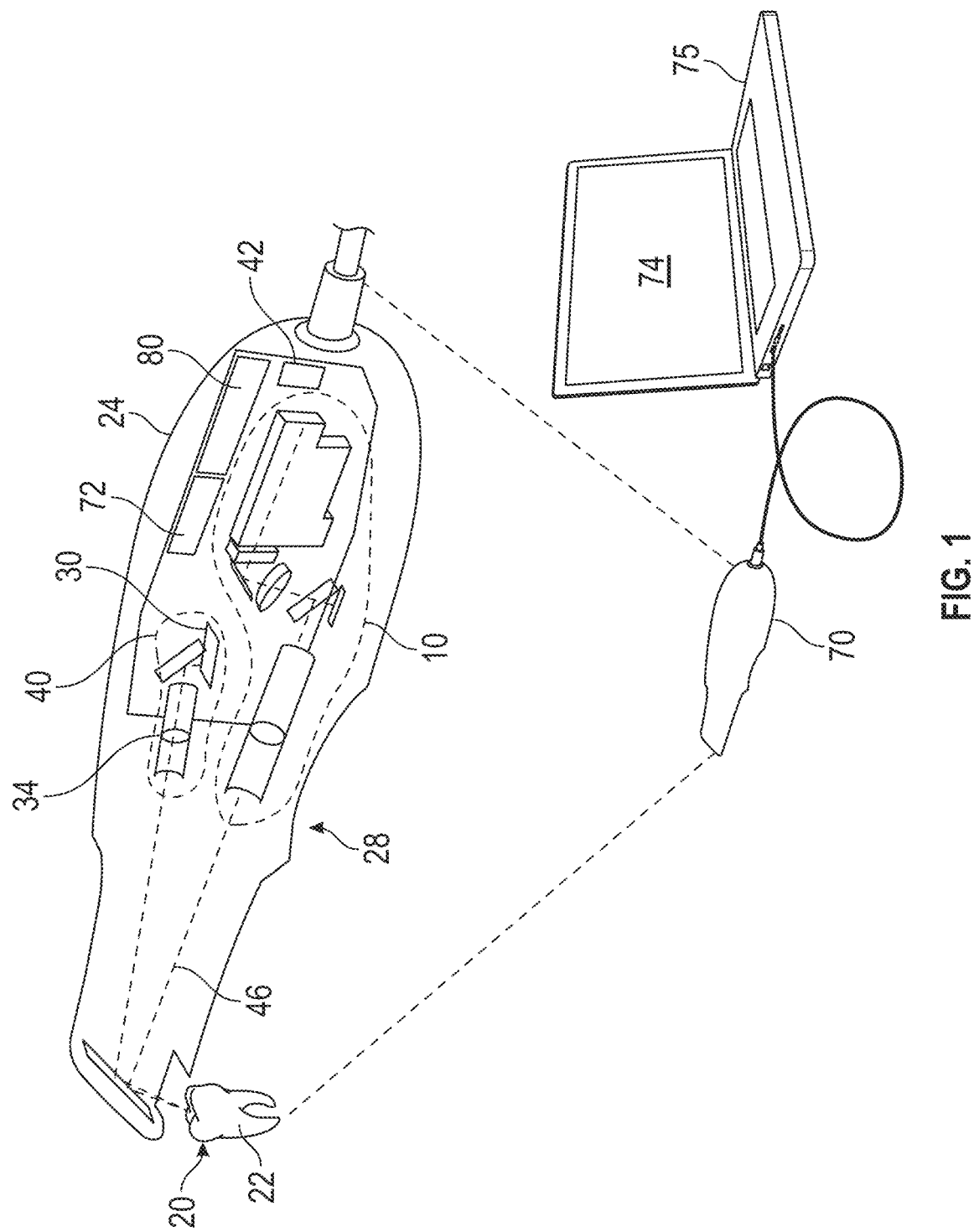
FIG. 1 is a schematic diagram that shows an intraoral camera.

The following is a description of exemplary method and/or apparatus embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2-D digital image from reflected visible or NIR (near-infrared) light, such as structured light that is reflected from the surface of teeth and supporting structures; in addition, the camera can operate in single-image mode or a continuous acquisition or video mode. In the context of the present disclosure, the terms "camera" and "scanner" can be used interchangeably to describe the same device, since the device can obtain different image types.

The term "subject" refers to the tooth or other portion of a patient that is being imaged and, in optical terms, can be considered equivalent to the "object" of the corresponding imaging system. The term "lens" can be used to identify a single-element lens or a lens group, such as a doublet or other arrangement in which lenses are positioned adjacently, for example.

The phrase "at or near" for placement of an optical component describes component placement at a position along an optical path where it performs its intended function, within tolerances acceptable in optical fabrication practice. Placement of a phase modulator near the optical stop means positioning the phase modulator at a position close enough to the stop to provide suitable phase modulation to yield an extended depth of field for imaging, as described in more detail subsequently. For a hand-held optical imaging apparatus, a position that is at least within a few mm of the stop can be sufficient for positioning an optical phase modulator.

In the context of the present disclosure, a reflectance image is a 2D image of a subject obtained by illuminating the subject with a field of light and obtaining the reflected light from the subject. A reflectance image can be monochrome or polychromatic and can use full field illumination or patterned light, such as for surface contour characterization. A polychromatic reflectance image can be obtained using a monochrome sensor with illumination fields of different colors, that is, of different wavelength bands.

FIG. 1 is a schematic diagram showing an imaging apparatus 70 that can operate as a still image or video camera 24 for polychromatic reflectance image data capture as well as a scanner 28 for projecting and imaging functions that characterize surface contour using structured light patterns 46. A handheld imaging apparatus 70 can use camera 24 for image acquisition for both contour scanning and image capture functions according to an embodiment of the present disclosure.

As shown in FIG. 1, a control logic processor 80, or other type of computer may be part of camera 24, controlling the operation of an illumination array 10 that generates the structured light and directs the light toward a surface position and controlling operation of an imaging sensor array 30. Image data from a surface 20, such as from a tooth 22, is obtained from imaging sensor array 30 and stored as image data in a memory 72. Imaging sensor array 30 is part of a sensing apparatus 40 that includes a lens assembly 34 and associated elements for acquiring image content. Control logic processor 80, in signal communication with camera 24 components that acquire the image, processes the received image data and stores the mapping in memory 72. The resulting image from memory 72 is then optionally rendered and displayed on a display 74, which may be part of another computer 75 used for some portion of the processing described herein. Memory 72 may also include a display buffer. One or more sensors 42, such as a motion sensor, can also be provided as part of scanner 28 circuitry. The image sensor array 30 can be a charge-coupled device (CCD) or a complementary metal oxide semiconductor (CMOS) array, for example.

In structured light imaging, a pattern of lines or other shapes is projected from illumination array 10 toward the surface of an object from a given angle. The projected pattern from the illuminated surface position is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of structured light imaging, used in order to complete the contour mapping of the surface and to increase overall resolution in the contour image.

Figure 2:
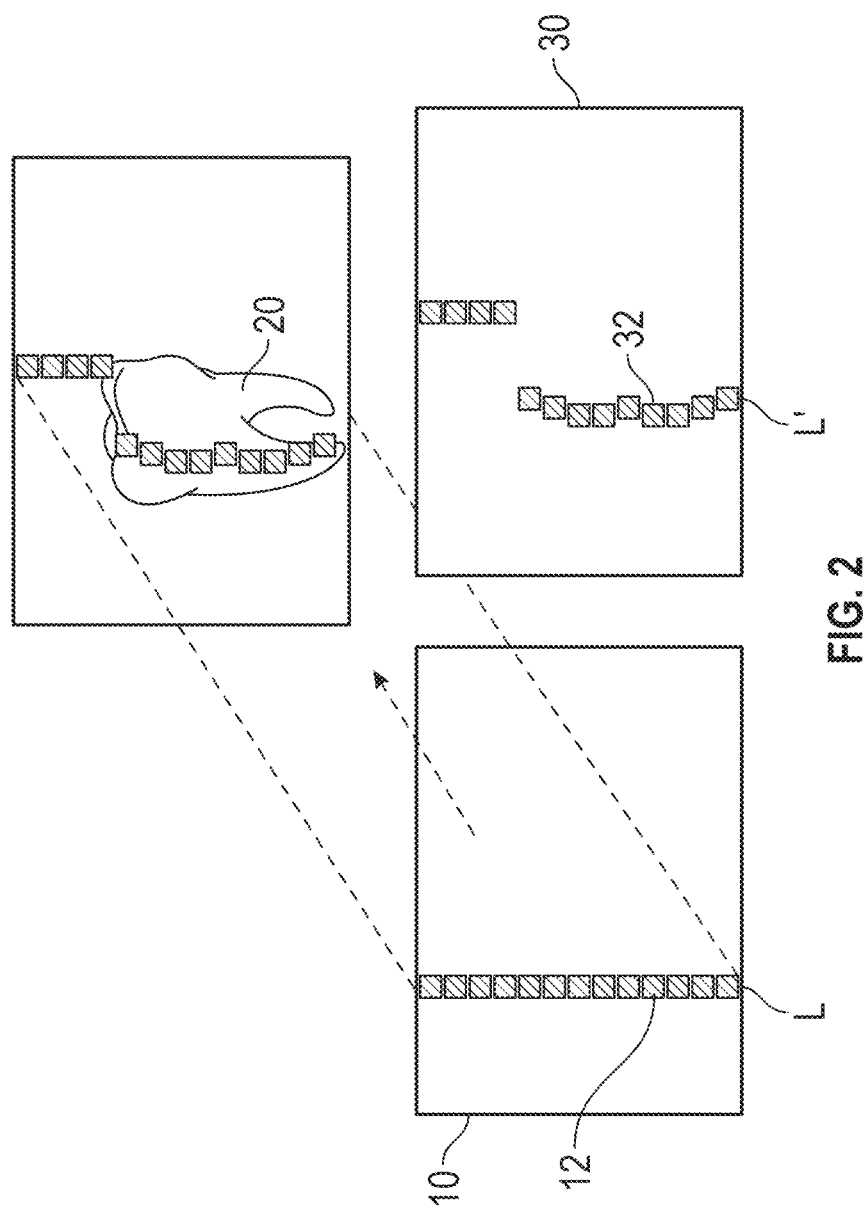
FIG. 2 is a schematic diagram that shows the use of patterned light for characterizing surface contour.

The schematic diagram of FIG. 2 shows, with the example of a single line of light L, how patterned light is used for obtaining surface contour information by a scanner using a handheld camera or other portable imaging device. A mapping is obtained as an illumination array 10 directs a pattern of light onto a surface 20 and a corresponding image of a line L' is formed on an imaging sensor array 30. Each pixel 32 on imaging sensor array 30 maps to a corresponding pixel 12 on illumination array 10 according to modulation by surface 20. Shifts in pixel position, as represented in FIG. 2, yield useful information about the contour of surface 20. It can be appreciated that the basic pattern shown in FIG. 2 can be implemented in a number of ways, using a variety of illumination sources and sequences for light pattern generation and using one or more different types of sensor arrays 30. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the light pattern as needed for the mapping sequence.

By projecting and capturing images that show structured light patterns that duplicate the arrangement shown in FIG. 2 multiple times, the image of the contour line on the camera simultaneously locates a number of surface points of the imaged object. This speeds the process of gathering many sample points, while the plane of light (and usually also the receiving camera) is laterally moved in order to "paint" some or all of the exterior surface of the object with the plane of light.

A synchronous succession of multiple structured light patterns can be projected and analyzed together for a number of reasons, including to increase the density of lines for additional reconstructed points and to detect and/or correct incompatible line sequences. Use of multiple structured light patterns is described in commonly assigned U.S. patent application Publications No. US2013/0120532 and No. US2013/0120533, both entitled "3D INTRAORAL MEASUREMENTS USING OPTICAL MULTILINE METHOD" and incorporated herein in their entirety.

Figure 3:
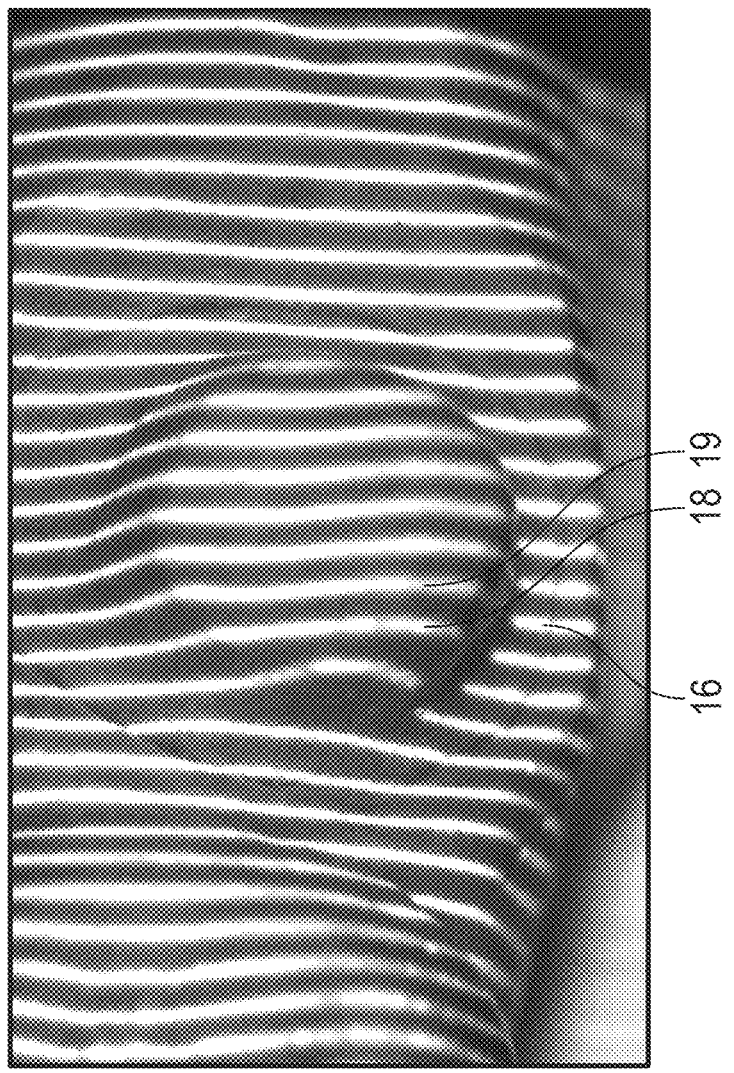
FIG. 3 shows surface imaging using a pattern with multiple lines of light.

FIG. 3 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult over portions of the surface to determine whether line segment 16 is from the same line of illumination as line segment 18 or adjacent line segment 19. If line features are blurred or defocused, it can be much more difficult to identify and trace line segments.

The thin lens equation provides an idealized approximation of object distance (O) and image distance (I) for a focal length $f$:

$$\frac{1}{I} = \frac{1}{f} - \frac{1}{O} \qquad (1)$$

Applying the relationship shown in (1), it can be appreciated that the image distance I shifts when the object distance O changes. The defocus wave-front aberration that is caused by such an image shift corresponds to:

$$W = \frac{(I_1 - I_2)}{8(F/\#)^2} \qquad (2)$$

Given the relationship shown in (2), it can be appreciated that one solution for decreasing the defocus aberration W is increasing the F/# value, such as by using a smaller aperture. However, the use of a smaller aperture further reduces the illumination in a light-starved system and may also decrease camera resolution.

Certain exemplary method and/or apparatus embodiments of the application describes a solution for decreasing defocus aberration in the optical path using phase manipulation or wavefront coding. Wavefront coding inserts a phase-mask modulator, phase plate modulator, or, simply, phase modulator, at the aperture or stop of the imaging system in order to modulate the wavefront form, effectively correcting misfocus of the image over a range of focal distances.

Figure 4:
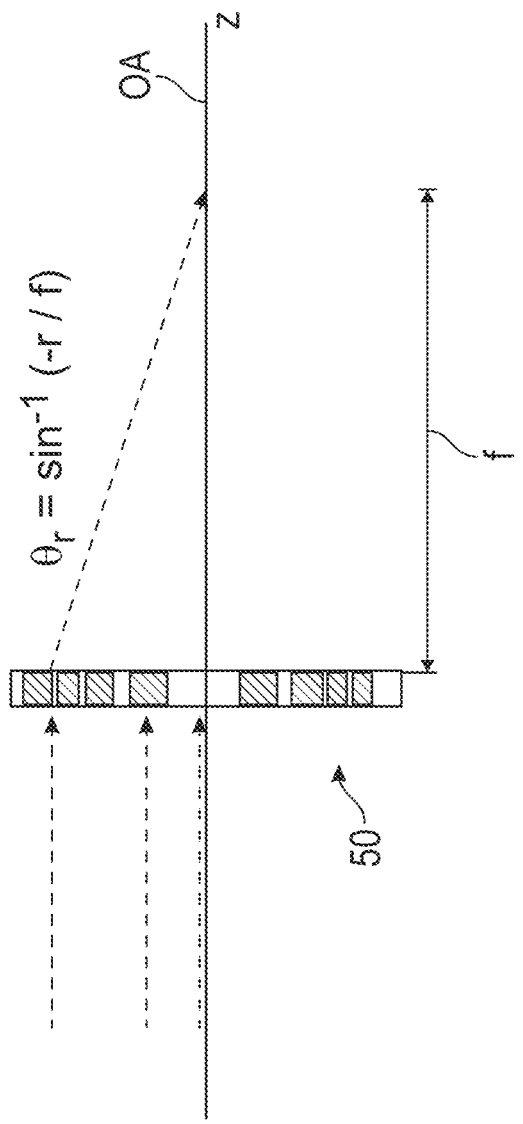
FIG. 4 shows a transparent phase plate that serves as a phase modulator.

The schematic view of FIG. 4 shows one type of transparent phase plate that has the following transmittance:

$$f(r) = e^{j\pi\left(\frac{r^2}{\lambda f}\right)} \qquad (3a)$$

This exemplary phase plate bends the plane wave position at r by an angle:

$$\theta_r = \sin^{-1}(-r/f) \qquad (3b)$$

With this behavior, a phase plate 50 can act like a spherical lens with focal length $f$. Phase plate 50 can have an arrangement of areas having different optical indices or thickness, for example.

One exemplary straightforward modulation function of the phase modulator as the phase plate 50 can be expressed as follows:

$$P(x,y) = a(x^3 + y^3) \qquad (4)$$

The coefficient $\alpha$ is determined by optimization, using techniques familiar to those skilled in the optical design art. The phase modulator can have various shapes such as being rectangular or circular in shape. The phase modulator can have different phase functions in one or multiple dimensions such as orthogonal x- and y-directions. The phase modulator can have symmetric or non-symmetric phase functions. Certain exemplary method and/or apparatus embodiments according to the application can provide a phase modulator to generate blurred images or a PSF (Point Spread Function) that is very similar at multiple focus distances and different field positions along the intraoral imaging apparatus optical axis. In exemplary embodiments, digital filters can be used to restore such blurred images at different (e.g., increased) focus distances.

Figure 5:
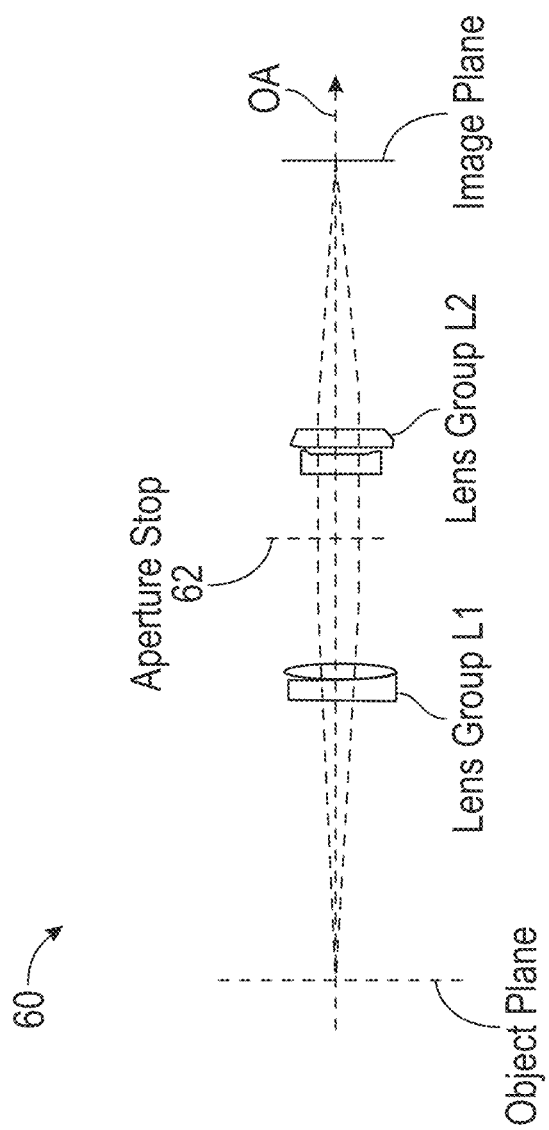
FIG. 5 shows schematic diagrams for an imaging lens system with a stop.

Referring to FIG. 5, an imaging lens system 60 with an aperture stop 62 can include two lenses or lens groups: an objective lens L1 preceding and a second lens L2 following the stop along optical axis OA. The imaging lens system of FIG. 5 can have the overall arrangement of a conventional 4-f (four focal length) imaging system. However, the geometrical focal distances do not rigidly constrain image quality when using the approach of the present disclosure. A phase modulator 50 (here, a transparency such as phase plate or phase mask) can be added to modulate the wave-front form at or near stop 62. This effectively enables the imaging system to obtain improved focus or clear images over a range (e.g., larger) of focal distances.

In practice, the transmittance function $f(r)$ for perfect focus could be highly complex and difficult to manufacture; it is even possible that no ideal transmittance function solution can be found. Phase plate or phase modulator 50 (FIG. 4), however, need not provide perfect focus at any location. Instead, phase modulator 50 can be positioned at or near the stop 62 (FIG. 5) in order to obtain a well-defined, uniform PSF (Point Spread Function) that is very similar at multiple distances along the optical axis OA. Then, since the PSF is well-defined and very similar PSF characteristics apply over a range of distances, in one exemplary embodiment the same digital restoration filtering can be used for correcting misfocus.

According to some exemplary embodiments of the application, the phase mask or other phase modulator 50 can be a rectangular phase plate with non-symmetric free-form, a circular phase plate with symmetric free-form or the like. The imaging system with a phase modulator 50 added is designed or optimized to provide PSFs at different object distances and field positions, wherein the different PSFs preferably exhibit a high degree of similarity and are of generally small size. Coefficients of the free-form surface of the phase mask or other type of phase modulator can be defined according to this design or optimization. Various aberrations are considered in the optimization; clear images can be restored using a digital filter.

It should be noted that the stop need not be between two lenses or lens groups, as shown for stop 62 in the exemplary configuration of FIG. 5. In some imaging optics systems, the stop can be at some other location along the optical axis OA.

Reference is hereby made to the following:

Edward R. Dowski, Gregory E. Johnson, "Wavefront Coding: A modern method of achieving high performance and/or low cost imaging systems" CDM Optics, Inc., Boulder, Colo., pp. 1-9.

Manjunath Somayaji, Vikrant R. Bhakta, and Marc P. Christensen, "Experimental evidence of the theoretical spatial frequency response of cubic phase mask wavefront coding imaging systems", Optics Express, vol. 20, no. 2, 16 Jan., 2012. pp. 1878-1895.

Hsin-Yueh Sung, Sidney S. Yang, Horng Chang, "Design of Mobile Phone Lens with Extended Depth of Field Based on Point-spread Function Focus Invariance" *Proc. of SPIE* Vol. 7061, pp. 706107-1, 706107-11.

Tingyu Zhao, Thomas Mauger, and Guoqiang Li, "Optimization of wavefront-coded infinity-corrected microscope systems with extended depth of field", *Biomedical Optics Express*, 31 Jul. 2013, pp. 1464-1471.

Sara Bradburn, Wade Thomas Cathey, and Edward R. Dowski, Jr. "Realizations of Focus Invariance in Optical/Digital Systems with Wavefront Coding", Imaging Systems Laboratory, Optoelectronic Computing Systems Center, Dept. of Electrical and Computer Engineering, University of Colorado at Boulder. pp. 1-22.

Edward R. Dowski, Jr. and Wade Thomas Cathey, "Extended Depth of Field Through Wave-front Coding" *Applied Optics*, vol. 34, No. 11, 10 Apr. 1995, pp. 1859-1866.

Figures 6A, 6B:
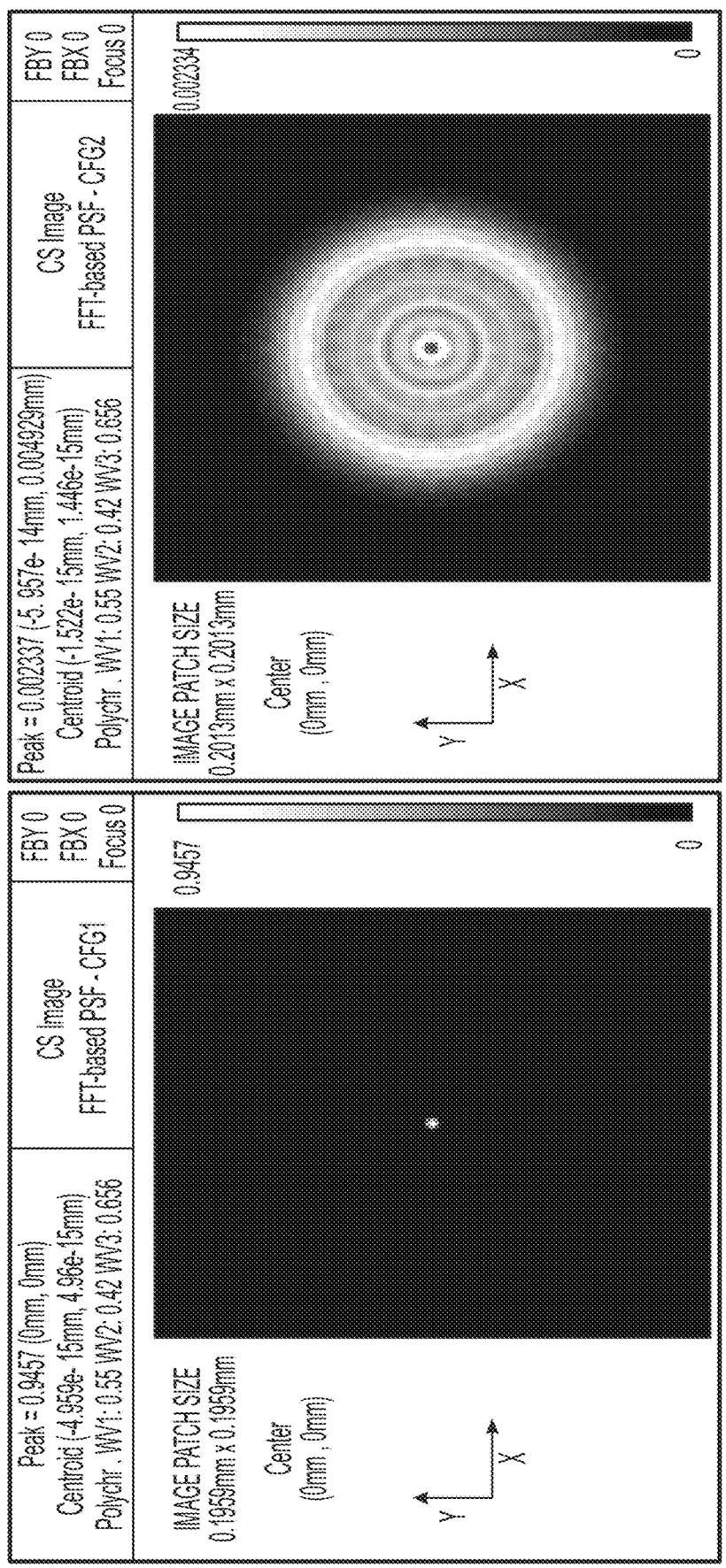
FIGS. 6A, 6B, and 6C show point spread functions (PSFs) for the imaging system of FIG. 5, but without phase modulation.
Figures 6C, 7A:
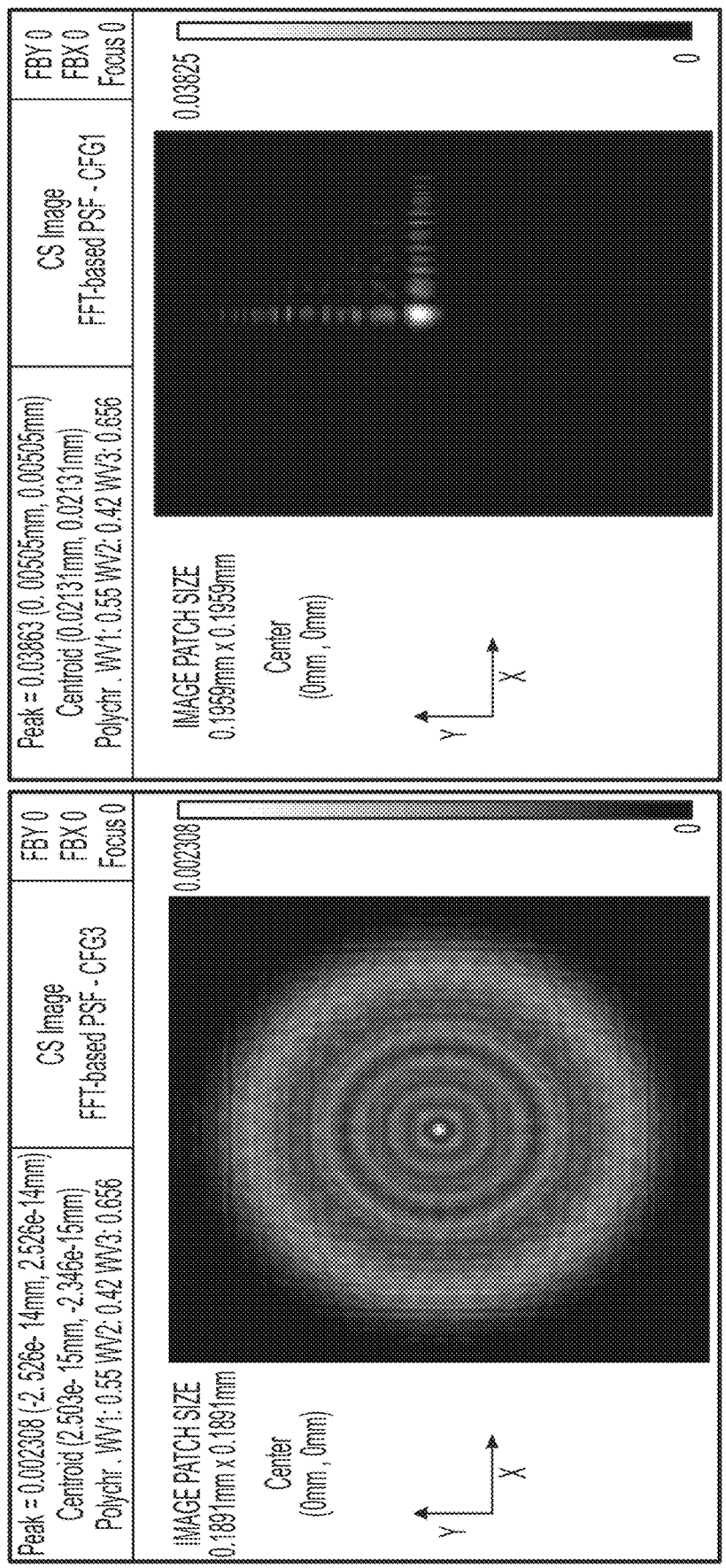
FIGS. 7A, 7B, and 7C show PSFs for the imaging system of FIG. 5 using a phase mask modulator according to an embodiment of the present disclosure.

By way of example, FIGS. 6A, 6B, and 6C show PSFs for the imaging system of FIG. 5 without phase modulation at stop 62. FIG. 6A shows the PSF for a point source at the focal plane of the imaging lens system. FIG. 6B shows the PSF for the point source object advanced +12 mm from the focal point, clearly showing an out-of-focus condition. FIG. 6C shows the PSF with the point source object at −12 mm from the focal point, yielding an even more pronounced mis-focus. From the example PSFs of FIGS. 6A-6C, it is clear that, in the absence of phase modulator 50, only when an object is positioned at or near the object focal plane is the imaging system likely to provide an acceptable image.

Figures 7B, 7C:
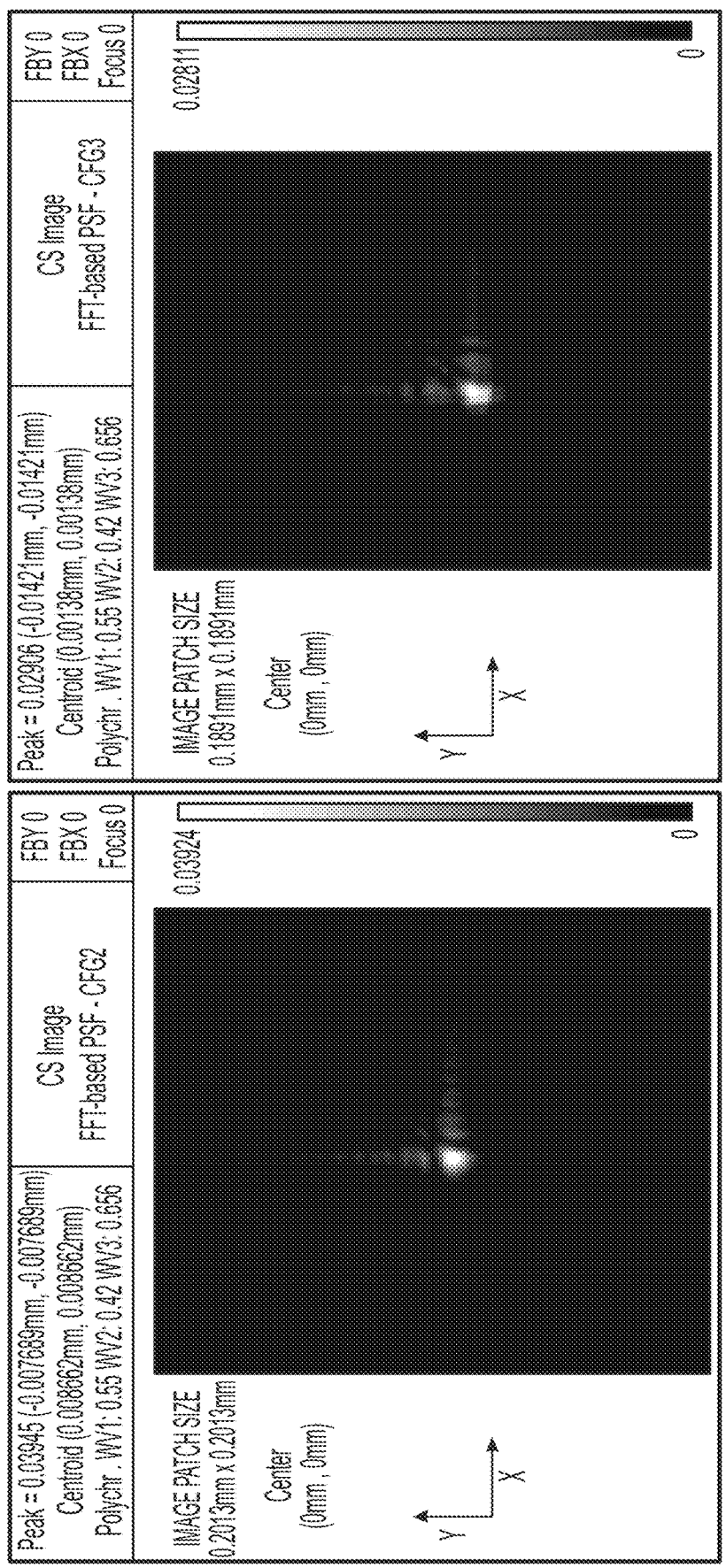

FIGS. 7A, 7B, and 7C show PSFs for the imaging system of FIG. 5 using phase modulator 50. The focal distances in FIGS. 7A-7C correspond to distances in FIGS. 6A-6C, that is, with the point source object at 0, +12 mm, and −12 mm from focus, respectively. Noticeably, the PSF distribution shown over this range is not the ideal PSF for focus as in FIG. 6A. However, the PSF energy distribution, which can be termed the PSF characteristic, is very nearly the same when the focal distance is varied over an appreciable distance. This means that the same digital filtering can be used for image correction; that is, the same digital filtering can be applied for deblurring the image whether the object is +12 mm out of focus, in focus, or −12 mm out of focus. In one exemplary embodiment, different digital filtering can be applied to different defocusing distances.

Figure 8:
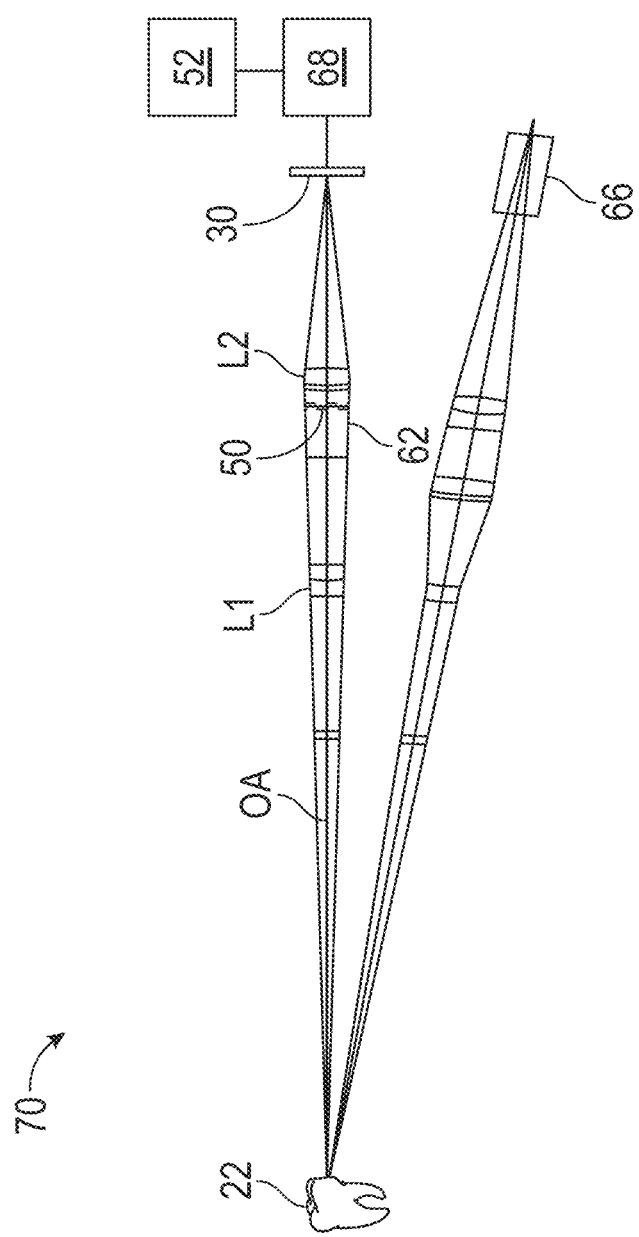
FIG. 8 is a schematic diagram that shows illumination and imaging optical paths for an imaging apparatus configured to provide an extended depth of field (DOF).

The schematic view of FIG. 8 shows exemplary illumination and imaging optical paths for imaging apparatus 70 of FIG. 1, configured to provide an extended depth of field (DOF). An illumination source 66 directs light to tooth 22 through an illumination path. Phase modulator 50 is disposed at the stop 62 in the imaging path, between lenses (or lens groups) L1 and L2. Sensor array 30 forms image data from the received light. An image processor 68 is in signal communication with sensor array 30. Image processor 68 is programmed with instructions to condition data from the image sensor array to correct for blurring in the received image and to provide conditioned image data that can be rendered on a display 52 that is in signal communication with processor 68. Digital processing by processor 68 can occur in real time, that is, as soon as the image data is acquired, allowing a practitioner or other operator to view processed imaging results as they are obtained, without perceptible delay for image processing, as long as processor 68 speed is sufficient. Illumination source 66 can include a solid-state light emitter, such as a light-emitting diode, for example.

Figure 9B:
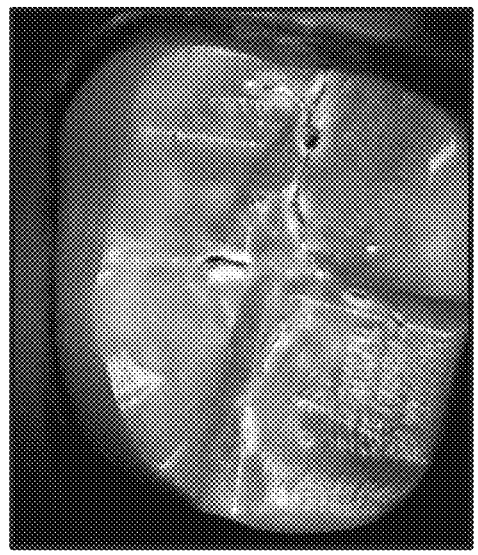
FIG. 9B shows the same image of FIG. 9A using phase modulation in the imaging path, after applying digital restoration as described herein.
Figure 9A:
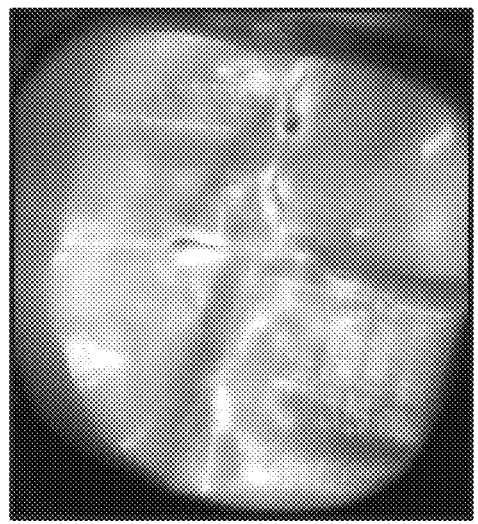
FIG. 9A shows an example of an image acquired at some distance from the focal plane of the imaging apparatus, using phase modulation in the imaging path, as described herein.

FIG. 9A shows an example of an image acquired at some distance from the focal plane of the imaging apparatus, using the phase modulator 50 as described previously. The slightly blurred image of FIG. 9A can be acquired at any number of distances on each side of the ideal object plane; in each case, over the extended DOF, the acquired image will look substantially the same as shown, requiring some amount of de-blurring. FIG. 9B shows the same image generated as described for FIG. 9A, but following application of a digital filter in accordance with an exemplary embodiment. The image has noticeably improved contrast, resolution, and/or dynamic range after digital image processing. Significantly in one exemplary embodiment, the same digital filtering algorithms can be applied for images captured over a range of focal distances.

In the imaging system of the 3D intra-oral camera without phase modulation, PSFs change at different object distances (FIGS. 6A, 6B, and 6C). In the imaging system with phase modulation added, PSFs are similar and keep a compact size at different object distances (FIGS. 7A, 7B, and 7C). The clear image can be restored by a digital processing filter.

Cubic Phase Plate as Phase Modulator

One non-symmetry free-form of phase plate is the cubic phase mask (CPM). The CPM provides straightforward design and inexpensive fabrication, and is robust. The modulation function of the CPM can be expressed as given in equation (4) above.

In the imaging system of a 3D intra-oral camera 24 of FIG. 1, PSFs change at different object distances, as was shown in the examples of FIGS. 6A-6C. By adding phase modulation, the Applicants have modified imaging system performance to allow similar PSFs over a range of object distances, as shown in the examples of FIGS. 7A-7C, with clear imaging capable of being restored using digital filtering, as described with reference to FIGS. 9A and 9B.

Blurred Image Restoration

A number of methods can be used to provide blurring correction, also termed de-blurring, for images obtained using the extended DOF of the present disclosure. The following gives a summary of theoretical background and basis for blurred image restoration.

For an imaging system with an incoherent source, the observed image Ui(xi, yi) is given by the standard image formation equation:

$$Ui(xi,yi) = \iint h(xi,yi;xo,yo)Uo(xo,yo)dxodyo + n(xo,yo); \quad (5)$$

Where Uo (xo, yo) is the object brightness distribution, h(xi, yi; xo, yo) is the point spread function (PSF) of the imaging system, n(xo, yo) is the noise term.

Fourier transformation to the frequency domain yields the following:

$$Ui(u,v) = H(u,v)Uo(u,v) + n(u,v); \quad (6)$$

Here, noise term n (u, v) is mainly from high frequencies, predominantly noise content, with some signal content. For some applications, clear images are mainly from the low frequency signals, such as multiline patterns for contour imaging using the 3D intra-oral camera of FIG. 1. One way to remove the noise term n(u, v) is to apply a high-frequency cut-off filter. Application of a high-frequency filter yields:

$$Ui(u,v) = \begin{cases} H(u,v)U0(u,v) & |u,v| < (u,v)\text{cutoff} \\ 0 & |u,v| > (u,v)\text{cutoff} \end{cases} \quad (7)$$

The object field in the spatial domain can be calculated as:

$$Uo(xo,yo) = FFT^{-1}[Ui(u,v)/H(u,v)]; |u,v| < (u,v)\text{cutoff} \quad (8)$$

As a result of this digital filter processing, blurring is corrected and clear images are restored.

Unsharp masking or other type of deblurring filter can alternately be used for image restoration.

Implementation Sequence

An implementation of the intra-oral imaging apparatus can be formed using the following sequence:
  (i) Begin with a standard imaging lens system having an aperture stop.
  (ii) Add a free-form phase modulator, such as a cubic phase plate to the aperture stop. The free-form phase plate can be expressed as a polynomial expression, such as the cubic phase $\alpha(x^3+y^3)$.
  (iii) The correlation operand of PSFs at different object distances and field positions are defined (with a user-defined operand) to get a high degree of similarity of PSFs at these distances and fields through optimization.
  (iv) A minimization operand of PSF size is defined to get a compact PSF size at different object distances and field positions through optimization. The reference PSF is PSF at field (0,0), and at the best focal distance of the standard imaging lens system.
  (v) Design an imaging lens system with a phase plate at its stop after optimization; determine appropriate polynomial coefficients of the phase plate.
  (vi) According to the resulting PSFs from optimization and the reference PSF, design a digital filter to restore blurred images. Steps of FIG. 10 form a suitable digital filter that can be integrated into the image processing logic.

Steps of FIG. 10 show a sequence for forming a suitable digital filter, applying techniques known to those skilled in the image processing art. A measurement step S100 measures PSFs at the desired focal distances and fields. The PSFs can then be averaged or otherwise combined. An inversion step S110 then inverts the averaged PSF and performs a Fourier transform to the frequency domain. A multiplication step S120 then multiplies the PSF function by a high-frequency cutoff filter. A second inversion step S130 performs an inverse Fourier transform back to the spatial domain, which forms a clear image. A filter forming step S140 then forms a single digital filter from results of this processing.

Digital filtering can not only correct image blurring due to defocus, but can also correct or remedy other aberrations such as spherical aberration and coma, for example.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present disclosure can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

Certain exemplary method and/or apparatus embodiments according to the application can increase a depth of focus for an intraoral imaging apparatus. Further, fluorescence imaging can be used with exemplary embodiments of the application. Exemplary embodiments according to the application can include various features described herein (individually or in combination).

While the invention has been illustrated with respect to one or more implementations, alterations and/or modifications can be made to the illustrated examples without departing from the spirit and scope of the appended claims.

In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An apparatus for intraoral imaging comprising:
   a) an illumination source including an illumination array and a lens assembly that directs imaging light along an illumination path to an object;
   b) an imaging apparatus that forms an image at an image sensor array from reflected imaging light from the object, the imaging apparatus having an optical stop along an optical axis, wherein pixels of the image sensor array are mapped to pixels of the illumination array;
   c) a transparent phase modulator disposed at or near the optical stop to generate a uniform point spread function (PSF) at multiple focal distances and different field positions along the optical axis; and
   d) an image processor that applies uniform digital restoration filtering based on a PSF characteristic to data at different focus distances from the image sensor array and provides processed image data of the object,
   wherein the PSF characteristic is an energy distribution of the uniform PSF.

2. The apparatus of claim 1 wherein the image processor provides deblurring of the image data.

3. The apparatus of claim 1 wherein the optical stop is between an objective lens that directs the reflected light through the optical stop and a second lens that directs light from the optical stop to the image sensor array.

4. The apparatus of claim 1 further comprising a display for rendering the processed image data, wherein the processed image data corresponds to contour images generated with patterned illumination.

5. The apparatus of claim 1 wherein the phase modulator is a cubic phase modulator.

6. The apparatus of claim 1 wherein the phase modulator, from a view along the optical axis, is rectangular or circular in shape.

7. The apparatus of claim 1 wherein the phase modulator has different phase functions in orthogonal x- and y-directions.

8. The apparatus of claim 1 wherein the illumination source includes a solid-state light emitter.

9. The apparatus of claim 1 wherein the image sensor array is a color or monochromatic device, wherein the processed image data corresponds to still images, video images, or 3D surface contours generated using structured light patterns.

10. The apparatus of claim 1 wherein the illumination source generates patterned illumination for surface contour imaging of the object.

11. The apparatus of claim 1 wherein the uniform PSF is determined by averaging an actual PSF measured at each of the multiple focal distances.

12. The apparatus of claim 1 wherein the uniform PSF is based on a transmittance function of the transparent phase modulator.

13. The apparatus of claim 1 wherein the illumination array and the image sensor array have a prescribed 3D spatial relationship.

14. An apparatus for intraoral imaging comprising:
   a) an illumination source including an illumination array and a lens assembly that directs imaging light along an illumination path to a n object;
   b) an imaging apparatus that forms an image from reflected imaging light from the object at an image sensor array, the imaging apparatus having an optical stop along an optical axis between an objective lens that directs the reflected light through the optical stop and a second lens that directs light from the optical stop to the image sensor array, wherein pixels of the image sensor array are mapped to pixels of the illumination array;
   c) a transparent phase modulator disposed at or near the optical stop to generate a uniform point spread function (PSF) at multiple focal distances and different field positions along the optical axis;
   d) an image processor that is programmed with instructions to apply a uniform digital restoration filter based on a PSF characteristic to data at different focus distances from the image sensor array for deblurring according to phase function characteristics of the phase modulator; and provides processed image data of the object; and
   e) a display in signal communication with the image processor for rendering the processed image data,
   wherein the PSF characteristic is an energy distribution of the uniform PSF.

15. The apparatus of claim 14 wherein the phase modulator is a cubic phase plate to increase a depth of focus for the intraoral imaging apparatus.

16. An intraoral imaging method comprising:
   a) directing light along an illumination path to an object from an illumination source including an illumination array and a lens assembly;
   b) directing reflected light from the object along an optical axis through an objective lens of the lens assembly that directs the reflected light through an optical stop;
   c) disposing a transparent phase modulator along the optical axis, at or near the optical stop to generate a uniform point spread function (PSF) at multiple focal distances and different field positions along the optical axis;
   d) forming image data at an image sensor array from the imaged reflected light from the object, wherein pixels of the image sensor array are mapped to pixels of the illumination array;
   e) applying uniform digital restoration filtering based on a PSF characteristic to the image data at different focus distances for deblurring; and
   f) rendering the restored image data on a display,
   wherein the PSF characteristic is an energy distribution of the uniform PSF.

17. The method of claim 16 wherein the optical stop is positioned between the objective lens and a second lens, and where the phase modulator causes the imaging system to have similar point spread functions over a range of object distances.

18. The method of claim 16 wherein conditioning the data for deblurring comprises digitally filtering the data based on a single point spread function.

\* \* \* \* \*

UNITED STATES PATENT AND TRADEMARK OFFICE
CERTIFICATE OF CORRECTION

PATENT NO. : 11,497,392 B2
APPLICATION NO. : 17/204332
DATED : November 15, 2022
INVENTOR(S) : Yiyi Guan, Victor C. Wong and James R. Milch Page 1 of 1

It is certified that error appears in the above-identified patent and that said Letters Patent is hereby corrected as shown below:

In the Claims

Claim 14, Column 12, Line 13, "illumination path to a n object" should read --illumination path to an object--

Signed and Sealed this
Sixth Day of May, 2025

Coke Morgan Stewart
*Acting Director of the United States Patent and Trademark Office*